United States Patent

Lorenz et al.

Patent Number: 5,741,911
Date of Patent: Apr. 21, 1998

[54] BENZIMIDAZOLE-ISOINDOLENINE DYESTUFFS

[75] Inventors: Manfred Lorenz, Köln; Klaus-Wilfried Wanken, Leverkusen, both of Germany

[73] Assignee: Bayer Aktiengesellschaft, Leverkusen, Germany

[21] Appl. No.: 753,548

[22] Filed: Nov. 26, 1996

[30] Foreign Application Priority Data

Dec. 6, 1995 [DE] Germany ............... 195 45 464.2

[51] Int. Cl.$^6$ ............... C07D 235/04; C09B 57/00
[52] U.S. Cl. ............... 548/305.1; 8/526; 8/638; 8/648; 8/922; 524/93
[58] Field of Search ............... 548/305.1; 8/526, 8/638, 648, 922; 524/93

[56] References Cited

U.S. PATENT DOCUMENTS

| | | | |
|---|---|---|---|
| 3,646,033 | 2/1972 | Leister et al. | 260/250 |
| 4,051,099 | 9/1977 | von der Crone | 260/40 |
| 5,484,901 | 1/1996 | Krapp et al. | 534/741 |

OTHER PUBLICATIONS

Abstract of FR. 1537299; 5:General Organic–p. 2; French 1968–vol. 8, No. 41.

Primary Examiner—Fiona T. Powers
Assistant Examiner—Laura L. Stockton
Attorney, Agent, or Firm—Sprung Kramer Schaefer & Briscoe

[57] ABSTRACT

Benzimidazole-isoindolenines of the formula (I)

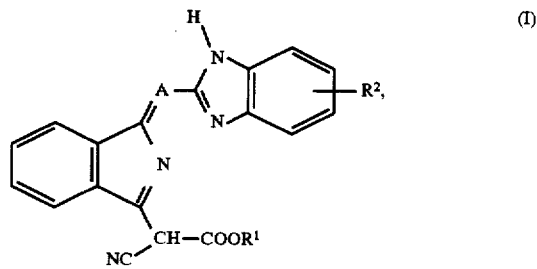

wherein
A represents N or a cyanomethylene radical,
$R^1$ represents a saturated or unsaturated, optionally substituted aliphatic radical having 4 to 20 C atoms, in particular 5 to 8 C atoms, which is optionally interrupted by one or more oxygen atoms and
$R^2$ denotes hydrogen, halogen, in particular Cl and Br, $C_1$-$C_4$-alkyl, a saturated or unsaturated aliphatic oxyradical having 1 to 4 C atoms which is optionally substituted by $C_1C_4$-alkoxy, CN or $NO_2$, $R^2$ not being hydrogen if $R^1$ represents n-butyl,
are outstandingly suitable for dyeing fully synthetic or semi-synthetic high molecular weight substances, in particular fiber materials, such as polyester.

14 Claims, No Drawings

BENZIMIDAZOLE-ISOINDOLENINE DYESTUFFS

The invention relates to benzimidazole-isoindolenine dyestuffs, processes for their preparation and their use for dyeing hydrophobic synthetic materials.

Benzimidazole-isoindolenine dyestuffs similar to those of the formula (I) are already known from DE-A 16 70 748, but these have disadvantages either in respect of their use or in respect of their processing. Disadvantages in respect of their use are to be understood as meaning, for example, too low an affinity or build-up capacity in the dyeing of polyester or poor light-fastness, in particular fastness to hot light, such as is required when textiles dyed with these dyestuffs are used in the automobile sector.

In particular, the dyestuff known from Example 1 from DE-A 16 70 748, which corresponds to the formula (I) if $R^2$ were to denote H, $R^1$ were to denote $C_2H_5$ and A were to denote N, has such disadvantages.

Disadvantages in respect of their processing are to be understood as meaning, in particular, poor dispersibility and grindability, which makes use for dyeing considerably more difficult.

For example, the dyestuff obtained according to FR-A 1 537 299 (Example 85), which corresponds to the following formula (I) if A were to represent cyanomethylene, $R^1$ were to represent n-butyl and $R^2$ were to represent hydrogen, has such disadvantages.

Benzimidazole-isoindolenines which correspond to the formula I or tautomeric forms thereof

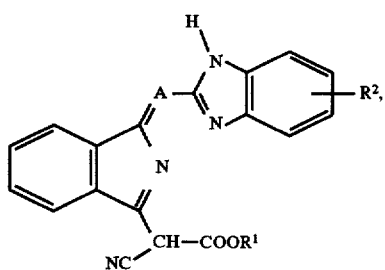

(I)

wherein

A represents N or a cyanomethylene radical, $R^1$ represents a saturated or unsaturated, optionally substituted aliphatic radical having 4 to 20 C atoms, in particular 5 to 8 C atoms, which is optionally interrupted by one or more oxygen atoms and $R^2$ denotes hydrogen, halogen, in particular Cl, F and Br, $C_1$-$C_4$-alkyl, a saturated or unsaturated aliphatic oxyradical having 1 to 4 C atoms, in particular $C_1$-$C_4$-alkoxy, which is optionally substituted by $C_1$-$C_4$-alkoxy, CN or $NO_2$, $R^2$ not being hydrogen if $R^1$ represents n-butyl, have been found.

Possible substituents which may be mentioned for the aliphatic radical in $R^1$ are, for example, CN, a saturated or unsaturated oxyradical having 1–4 C atoms, such as $C_1$-$C_4$-alkoxy, allyloxy and/or an acyloxy radical, such as α-acetoxyethyl.

Suitable radicals $R^1$ can be branched or straight-chain and are, for example, n-propyl, allyl, n-butyl, n-pentyl, n-hexyl, n-heptyl, n-octyl, n-decyl, 2-methoxy-ethyl, 2-ethoxy-ethyl, 2-butoxy-ethyl, 2-allyloxy-ethyl, 2-cyano-ethoxy-ethyl, 2-cyano-ethoxy-butyl, 2-acetoxy-ethyl, 3-ethoxy-1-propyl or 2-ethyl-hexyl. Possible branched radicals $R^1$ are preferably those having a methyl side chain, such as, for example, iso-pentyl, 1-methoxy-2-propyl, 1-ethoxy-2-propyl and 2-butoxy-butyl. The radicals n-butyl, n-pentyl and 2-butoxy-ethyl are especially preferred.

Preferred dyestuffs of the formula (I) are those which correspond to the formula (II) or tautomeric forms thereof

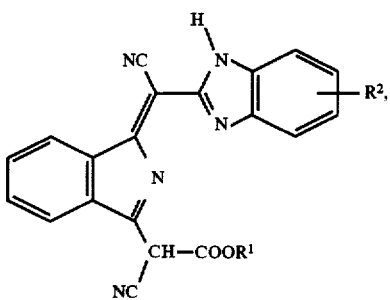

(II)

wherein $R^1$ represents a preferably straight-chain, saturated or unsaturated aliphatic radical having 5 to 8 C atoms, which is optionally substituted and/or interrupted by one or more oxygen atoms, and $R^2$ has the abovementioned meaning.

Preferably, $R^1$ represents n-amyl, n-hexyl, n-heptyl, n-octyl, 2-ethyl-hexyl, 2-methoxy-ethyl, 2-ethoxy-ethyl, 2-butoxy-ethyl, 3-methoxy-butyl or 1-methyl-2-methoxy-ethyl and $R^2$ represents hydrogen or methyl.

Dyestuffs of the formula (I) which are furthermore preferred are those which correspond to the formula (III) or tautomeric forms thereof

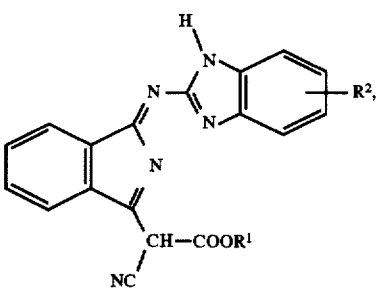

(III)

wherein $R^1$ and $R^2$ have the same general and preferred meanings as are given for the benzimidazoline-isoindolenines of the formula (II), $R^2$ not being hydrogen if $R^1$ represents n-butyl.

Although all the formulae described in this application represent only one—if several are conceivable—tautomeric form of the particular compound(s), they are representative of all conceivable tautomeric forms.

Furthermore, an E or Z isomer described by a formula, in particular in respect of the exocyclic double bond(s), also includes the other particular isomer. This applies unless expressly stated otherwise.

The invention furthermore relates to a process for the preparation of compounds of the formula (I), which is characterized in that a compound of the formula (IV)

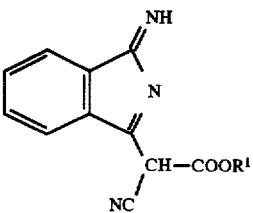

(IV)

is subjected to a condensation reaction with a benzimidazole of the formula (V)

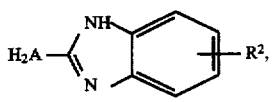

or an aminoisoindolenine of the formula (VI)

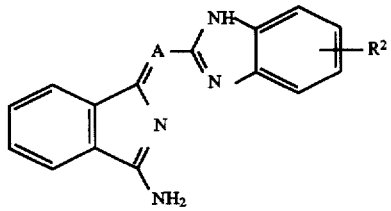

is subjected to a condensation reaction with a cyanoacetic acid ester of the formula (VII)

$$NC-CH_2-COOR^1 \quad (VII)$$

wherein $R^1$, $R^2$ and A have the abovementioned meaning.

In a preferred embodiment, the process according to the invention for the preparation of compounds of the formula (II) is carried out a) by condensation of compounds of the formula (VI) with benzimidazoles of the formula (V) which correspond to the formula (VIII)

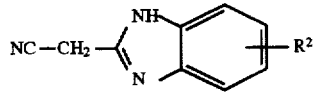

or b) by condensation of compounds of the formula (VI) which correspond to the formula (IX)

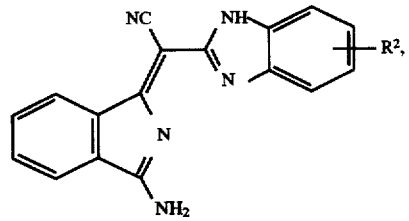

with cyanoacetic acid ester of the formula (VII), wherein the substituents $R^1$ and $R^2$ have the abovementioned meaning, characterized in that the process is carried out in a polar, in particular hydrophilic, organic solvent.

Examples of polar solvents which may be mentioned are: amides, such as dimethyl-formamide, formamide, dimethylacetamide and N-methylpyrrolidone, and furthermore dimethyl sulphoxide, acetonitrile, acetic acid or alcohol, the alcohol which is also used as the alcoholic component in the cyanoacetic acid esters of the formula (VII) preferably being employed. Moreover, mixtures of these solvents can also be used.

The condensation is in general carded out at temperatures from 20° to 150° C.

In a particularly preferred embodiment of this process, which is also to apply to the preparation of compounds of the formula (II) wherein $R^1$ denotes n-butanol and $R^2$ denotes hydrogen, the condensation is carded out in the presence of an organic acid.

This leads to an acceleration of the reaction, an improved crystallinity and a higher yield. Suitable organic acids which may be mentioned are, for example, lower aliphatic, saturated or unsaturated mono- or dicarboxylic acids, such as, for example, formic acid, acetic acid, propionic acid, butyric acid, oxalic acid, fumaric acid, maleic acid, succinic acid, glutaric acid, adipic acid, malic acid, lactic acid and citric acid, and also aromatic acids, such as, for example, benzoic acid and phthalic acid. The acids are added in amounts of 0.2 to 3 mol equivalents, preferably 1 to 2 mol equivalents, in each case based on the starting aminoisoindoline of the formula (IV) or (IX) which is to be employed. However, higher amounts of acid can also preferably be employed if the acid is to serve simultaneously as the solvent, such as, for example, acetic acid.

The advantage of this preferred procedure lies in the fact that by-products are for the most part avoided. Such by-products correspond, in particular, to the formula (X)

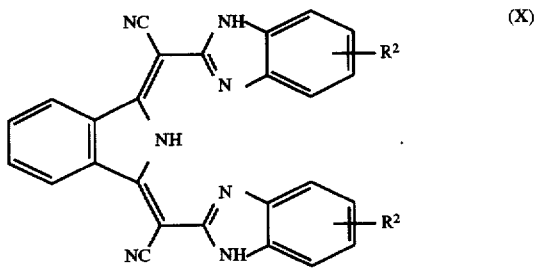

They are red and expensive to remove from the reaction mixture. The colour shade of the desired dyestuffs is therefore changed by a substantial content of (X). This disadvantage can be observed, for example, with the dyestuff prepared in FR-A-1 537 299, in Example 85.

In a particularly preferred embodiment of the process for the preparation of compounds of the formula (II) wherein $R^1$ can also represent n-butyl if $R^2$ denotes hydrogen, the reaction is carded out in water or an aqueous medium. In addition to the water, organic solvents can also be present here, and preferably those which are completely or partly miscible with water, such as, for example, alcohols, preferably the alcohols on which the radical $R^1$ is based, ketones, such as, for example, acetone, methyl ethyl ketone, cyclohexanone, ethers, such as tetrahydrofuran and dioxane, dimethylformamide, N-methylpyrrolidone and others. However, water-immiscible solvents can also be added to the aqueous reaction medium, for example in order to improve the crystallinity and to achieve particular crystal forms. The organic solvents can be present from the beginning, or can also be added only in the course of the reaction. Here also, addition of an organic acid may have an advantageous effect and lead to an acceleration of the reaction, an improved crystallinity and a higher yield.

Using water or aqueous reaction media facilitates isolation of the dyestuffs and avoids working up of relatively large quantities of organic solvents. Water contents of 20 to 100%, in particular 50 to 100% (based on the amount of reaction medium used), are preferably used in this process variant. This procedure is particularly preferred for route a), starting from compounds of the formula VIII.

If water or a predominantly aqueous medium is used as the reaction medium, surface-active substances, such as dispersing agents, emulsifiers and wetting agents, are expediently added. Possible such substances are the known nonionic, anionic and cationic auxiliaries. Such compounds are, for example, salts of alkylbenzenesulphonic acids, alkylphenolsulphonic acids and alkylnaphthalenesulphonic acids, condensation products of phenolsulphonic acids, formaldehyde and urea, ligninsulphonates and addition products of ethylene oxide and propylene oxide with alkanols, alkanediols, phenols, carboxylic acids, amines, carboxylic acid amides and their sulphuric acid half-esters, it also being possible to employ mixtures of these compounds. However, ligninsulphonates, such as, for example, kraft-lignins of the Reax type from Westvaco or sulphite-lignins of the Ufoxane type from Borregaard, are particularly preferred.

In an especially preferred process for the preparation of compounds of the formula (II) wherein $R^1$ can also represent n-butyl if $R^2$ denotes hydrogen, the condensation is carried out in accordance with route b) starting from the compound of the formula (IX)

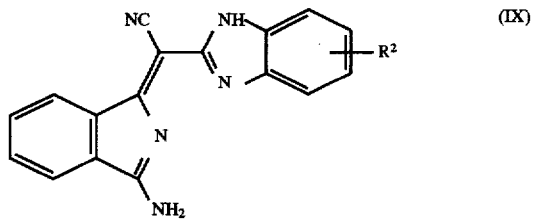

with cyanoacetic acid esters of the formula (VII) wherein $R^1$ and $R^2$ have the abovementioned meaning, at a temperature of 100° to 150° C., preferably at 110° to 130° C., in a polar organic solvent, such as are described above as examples, as the reaction medium and in the presence of an organic acid. In this case, the starting components are preferably employed in equimolar amounts. However, one component, preferably the cyanoacetic acid ester of the formula (VII), can also be employed in a 5 to 50%, preferably 10 to 30%, molar excess.

On the one hand very short reaction times and on the other hand very pure end products are realized in this manner.

The process variants described above are capable of keeping the content of unwanted by-products of the formula (X) significantly below 2%, preferably significantly below 1%.

A process variant which is furthermore preferred for the preparation of dyestuffs of the formula (I) wherein $R^1$ can also denote n-butyl if $R^2$ represents hydrogen is that in which the condensation is carried out starting from compounds of the formula (IV)

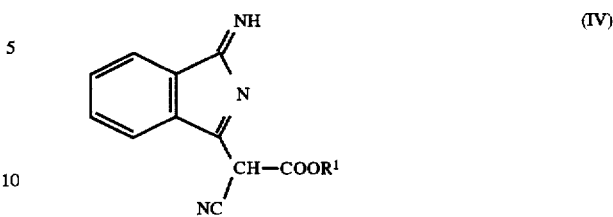

with benzimidazoles of the formula (VIII)

the condensation preferably being carried out at a temperature from 25° to 100° C.

A process for the preparation of compounds of the formula (II) which is likewise especially preferred is characterized in that the aminoisoindolenine compound of the formula (IV) or (IX) employed is prepared by condensation of amino-imino-isoindolenine of the formula (XI)

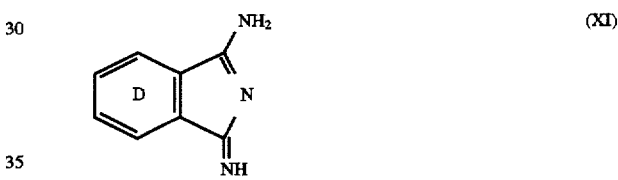

with the methine compounds of the formula (VII) or (VIII). This especially preferred process can be represented in the following equation:

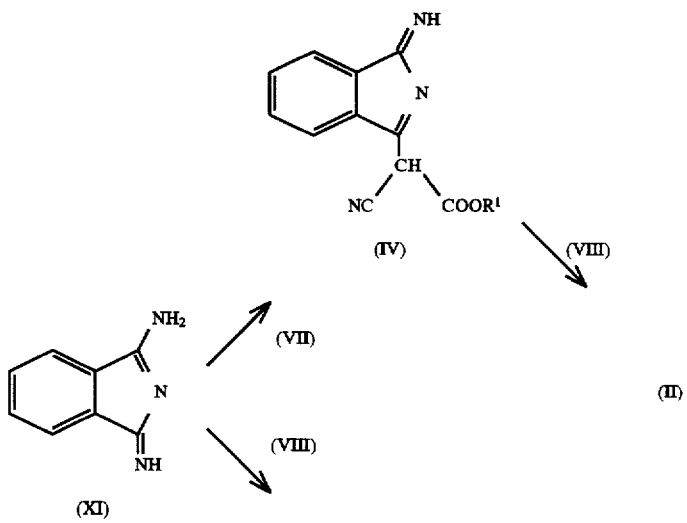

-continued

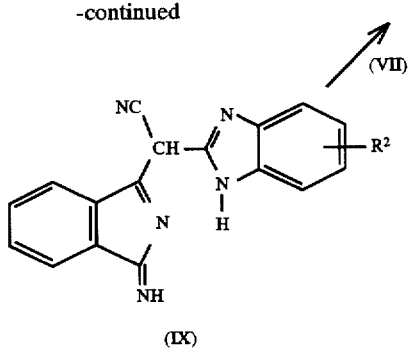

The above process for the preparation of dyestuffs of the formula (II), characterized in that the compound of the formula (IV) employed is obtained by reaction of the amino-imino-isoindoline compound of the formula (XI)

with a cyanoacetic acid ester of the formula (VII)

NC—CH$_2$—COOR$^1$   (VII), wherein R$^1$ has the above meaning,
or the compound of the formula (IX) employed is obtained by reaction of an amino-imino-isoindoline of the formula (XI) with a 2-cyanomethylbenzimidazole of the formula (VIII)

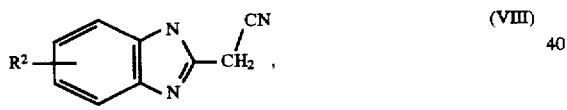

wherein R$^2$ has the above meaning, is accordingly preferred.

This process sequence according to the invention, starting from the amino-imino-isoindoline compounds of the formula (XI) to give dyestuffs of the formula (II) can preferably likewise be carried out in water or in an aqueous medium. A one-pot reaction, i.e. without intermediate isolation of the monocondensed compounds of the formula (VII) or (IX), is also possible, in particular, for this procedure.

The process for the preparation of compounds of the formula (III) is characterized in that compounds of the formula (VI) which correspond to the formula (XII)

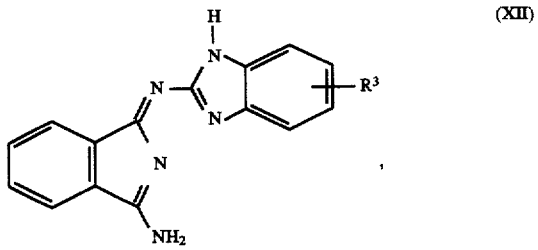

wherein R$^2$ has the above meaning, are subjected to a condensation reaction with cyanoacetic acid esters of the formula (VII)

NC—CH$_2$—COOR$^1$   (VII), wherein R$^1$ has the above meaning.

The preferred reaction conditions for this preparation process also apply to the preparation of compounds of the formula (III) wherein R$^1$ can represent n-butyl if R$^2$ represents hydrogen, and correspond to those for the preparation of compounds of the formula (II). Here also, it has been found, surprisingly, that the condensation reaction can be carried out under otherwise identical conditions, particularly advantageously in water or in mixtures of water with organic solvents. Preferred reaction temperatures are 60°–100° C.

Compounds of the formula (XII) can be prepared in various ways. Thus, on the one hand, amino-imino-isoindolenines of the formula (XI)

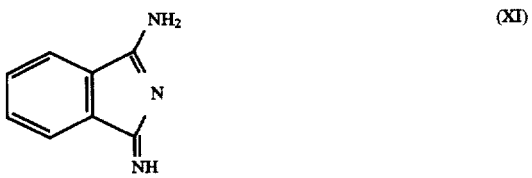

can be subjected to a condensation reaction with 2-aminobenzimidazoles of the formula (V) which correspond to the formula (XIII)

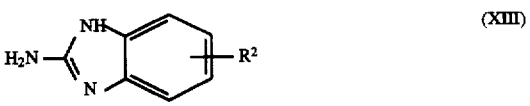

wherein R$^2$ has the above meaning. The condensation of (V) and (XI) to give (X) can be carried out by heating the components in an organic solvent, solvents which are employed being, for example, amides, such as formamide, dimethylformamide, dimethylacetamide and N-methylpyrrolidone, and preferably alcohols, in particular lower alcohols, such as methanol, ethanol, n-propanol and iso-propanol.

Another process has been found for the preparation of compounds of the formula (XII), which is characterized in that 2-aminobenzimidazoles of the formula (XIII)

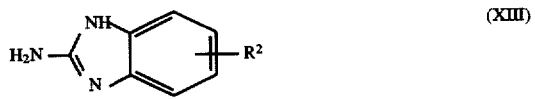

are reacted with phthalic acid dinitriles of the formula (XIV)

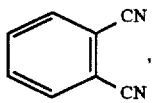
(XIV)

wherein $R^2$ has the above meaning, in the presence of a base.

This addition reaction can be carried out in an organic solvent, solvents which can be used being amides, such as, for example, formamide, dimethylformamide, dimethylacetamide and N-methylpyrrolidone, and preferably alcohols, and especially preferably lower alcohols, such as methanol, ethanol, n-propanol and iso-propanol. This reaction is preferably catalysed by alcoholates, such as sodium methylate, sodium ethylate and potassium tert-butylate. The mount of alcoholate can be varied within wide limits, but mounts of between 0.5 and 1 mol equivalent, based on the amount of (XIV) employed are preferred.

Suitable reaction temperatures are between 0° and 100° C., preferably between 20° and 60° C. The advantage of this process for the preparation of compounds of the formula (XII) is that the aminoiminoisoindolenine, which is usually likewise prepared from phthalic acid dinitrile, does not have to be prepared beforehand. Higher yields, in particular higher space-time yields, are therefore achieved, especially since this reaction proceeds very rapidly.

To overcome the disadvantages with respect to processing of the compound obtained in FR-A 1 537 299, Example 85, of the formula (XV)

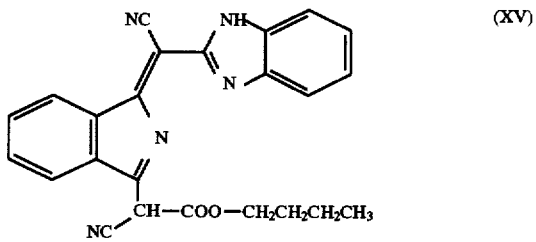
(XV)

new crystal modifications of (XV) which now no longer have the disadvantages described above have surprisingly been found.

In the processes known for the preparation of (XV) from FR-A-1 537 299, the condensation is carried out starting from the compound of the formula (XVI)

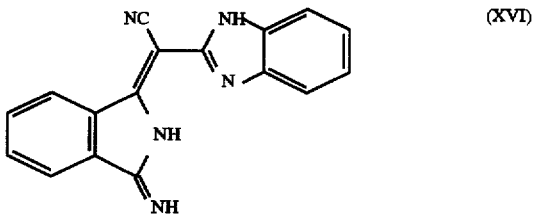
(XVI)

with n-butyl cyanoacetate (XVII) in nitrobenzene at a temperature of 180° C. The β-modification is formed in this reaction, and is characterized by the following moderate to intense reflections in the X-ray powder diagram, the data denoting the distance between lattice planes in Å and the relative intensities of the reflections in per cent (in parentheses). A computer-assisted Siemens D-500 powder diffractometer was used for the diffractograms, recorded with Cu-$K_\alpha$ radiation.

β-modification: 5.548 (70); 7.122 (100); 8.358 (70); 17.408 (91); 20.691 (53); 24.614 (54); 25.20 (55); 27.582 (65)

The β-modification can also be obtained if the condensation of (XVI) with (XVII) is carried out in n-butanol. It is typically obtained in the form of thread-like crystals which can be finished only with expense.

Surprisingly, further crystal modifications (α, γ, and ε) of (XV) which are very much easier to finish and therefore have surprising advantages in respect of processing have been found.

These modifications are characterized by moderate to intense reflections in the X-ray diffraction diagram by the following distances between lattice planes in Å with the associated relative intensities in per cent (in parentheses).

α-modification: 9.298 (100); 19.300 (12); 23.080 (14); 24.199 (20); 24.574 (36); 26.457 (85); 27.795 (23); 28.656 (16)

γ-modification: 5.007 (40); 5.474 (87); 6.316 (45.2); 8.393 (52); 10.045 (53); 16.646 (45); 25.772 (62); 26.377 (100)

ε-modification: 5.034 (50); 6.113 (100); 7.070 (29); 7.328 (25); 10.603 (33); 12.263 (23); 12.767 (21); 24.889 (24); 26.263 (30); 26.682 (23).

The invention furthermore relates to a process for the preparation of the compound of the formula (XV) in its γ-modification, characterized in that the condensation of (XVI) and (XVII) is carried out in dimethylformamide or another polar solvent, such as N-methylpyrrolidone or dimethyl sulphoxide, at a temperature of 60° to 140° C., or the product present in the co-modification is heated in such a solvent or recrystallized therefrom, the crystallization typically being carried out at temperatures below 80° C., preferably below 60° C.

The α-modification is obtainable, for example, by carrying out the reaction in n-butanol in the presence of aliphatic carboxylic acids, in particular aliphatic dicarboxylic acids, such as glutaric acid. The α-modification is obtained as compact crystals.

The process for the preparation of the ε-modification of the compound (XV) is characterized in that the condensation is carried out starting from the compound of the formula (XVIII)

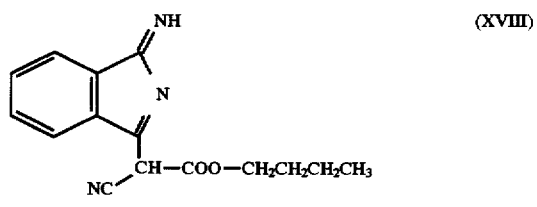
(XVIII)

with a compound of the formula (XIX)

(XIX)

in an aqueous medium.

The ε-modification is formed at temperatures from 60° to 100° C.

The formation of this ε-modification can be promoted here by heat treatment, and by addition of an organic solvent, preferably n-butanol, addition of organic acids, such as, for example, acetic acid, or addition of dispersing agents, it being possible for these measures to be used individually or in combination.

The invention furthermore relates to the use of dyestuffs of the formula (I) for dyeing fully synthetic or semi-synthetic high molecular weight substances. They are particularly suitable for dyeing or printing synthetic fibre materials, in particular those of aromatic polyesters and/or cellulose acetates. The dyeings obtained by this process have a high colour strength and show an outstanding light-fastness, in particular a high fastness to hot light, and are therefore particularly suitable for dyeing and printing textile materials for the automobile industry and for dyeing so-called microfibres.

Dyestuffs of the formula (I) are also outstandingly suitable for so-called thermo-transfer printing on textile and non-textile substrates, for example by the D2T2 (dye diffusion thermotransfer) process for image recording. The dyestuffs can furthermore be used for bulk dyeing of plastics, for example of polyethylenes, polypropylenes, polystyrene, polycarbonates and blends of plastics, such as, for example, ABS. The dyestuffs are fluorescent in some cases and are therefore also suitable as fluorescence dyestuffs. Preferred fluorescence dyestuffs here are dyestuffs of the formula (II).

Textile materials of polyester can be dyed with the dyestuffs according to the invention in the manner of spin dyeing, but preferably from aqueous suspension. For this, the dyestuffs are processed to dye preparations in a generally known manner, for example by grinding in water in the presence of dispersing agents and/or fillers. Using the preparations, if appropriate dried in vacuo or by atomizing, dyeing, padding or printing can be carried out in a so-called short or long liquor after addition of water.

To establish or improve the degree of dispersion, a surface-active agent or a mixture of such auxiliaries can be added during the grinding or the synthesis reaction. The particle size of the dyestuff particles can of course be influenced accordingly and adjusted to a required value by a grinding treatment, for example wet bead grinding, either during the synthesis or thereafter.

Possible dispersing agents are those of an anionic or non-anionic nature. In addition to dispersing agents of one or other group, it is also possible to employ dispersing agent mixtures, which means primarily mixtures of nonionic and anionic dispersing agents, since anionic and cationic dispersing agents tend to form precipitates when mixed with one another.

Anionic dispersing agents which have proved to be active in particular are condensation products of aromatic sulphonic acids with formaldehyde, such as condensation products of formaldehyde and alkylnaphthalenesulphonic acids or of formaldehyde, naphthalenesulphonic acids and benzenesulphonic acid, and condensation products of optionally substituted phenol with formaldehyde and sodium bisulphite.

Ligninsulphonates, for example those which are obtained by the sulphite or kraft process, are also particularly suitable. These are preferably products which are partly hydrolysed, oxidized, propoxylated or desulphonated, and fractionated by known processes, for example according to molecular weight or according to the degree of sulphonation. Mixtures of sulphite- and kraft-ligninsulphonates also have a good action.

Ligninsulphonates having an average molecular weight of between 1,000 and 100,000, a content of active ligninsulphonate of at least 80%, and preferably with a low content of polyvalent cations, are particularly suitable.

The degree of sulphonation can vary within wide limits.

Nonionic dispersing agents or emulsifiers are, for example, reaction products of alkylene oxides with alkylatable compounds, such as, for example, fatty alcohols, fatty amines, fatty acids, phenols, alkylphenols, arylalkylphenols, carboxylic acid amides and resin acids.

These are, for example, ethylene oxide adducts from the class of reaction products of ethylene oxide with:

a) saturated and/or unsaturated fatty alcohols having 6 to 20 C atoms; or b) alkylphenols having 4 to 12 C atoms in the alkyl radical, or c) saturated and/or unsaturated fatty amines having 14 to 20 C atoms, or d) saturated and/or unsaturated fatty acids having 14 to 20 C atoms, or e) hydrogenated and/or non-hydrogenated resin acids.

Ethylene oxide adducts which may be mentioned specifically are:

reaction products of saturated and/or unsaturated fatty alcohols having 6 to 20 C atoms with 5 to 30 mol of ethylene oxide, b) reaction products of alkylphenols having 4 to 12 C atoms with 5 to 20 mol of ethylene oxide, c) reaction products of saturated and/or unsaturated fatty acids having 14 to 20 C atoms with 5 to 20 mol of ethylene oxide.

Other preferred dispersing agents are alkoxylated styrene-phenol condensation products, which are optionally employed as a mixture with their inorganic esters which are obtained by reaction of the alkoxylated styrene-phenol condensation product with inorganic acids, such as, for example, amidosulphenic acid.

Mixtures of dyestuffs of the formula (I) are also particularly suitable for dyeing polyester, whereby the affinity and build-up capacity of the dyestuffs and their dispersibility can be improved under certain circumstances.

The novel dyestuff mixtures can be prepared by various processes:

1. by mixing the separately prepared and finished individual dyestuff components, 2. by finishing the separately prepared individual components together, 3. by synthesizing mixtures of two or more dyestuffs of the formula (I) from mixtures of different precursors together.

The dyestuffs are expediently mixed in suitable mills, for example ball or sand mills. However, separately finished individual dyestuffs can also be mixed by stirring into dye liquors.

Mixtures of dyestuffs of the formulae (II) and/or (III) which differ only in the radical $R^1$ are particularly suitable.

However, the dyestuffs are also outstandingly suitable for the preparation of mixtures with other disperse dyestuffs to produce brown, grey or green shades on the fibre, because they do not impair the light-fastness of these dyestuffs.

Another preferred embodiment of the present invention relates to mixtures of one or more of the dyestuffs of the formulae (I) to (III) with one or more dyestuffs such as are usually used for dyeing polyester fibres or polyester textile materials for automobile covering fabrics. These dyestuffs for dyeing automobile covering fabrics can be, in particular, azo, disazo, anthraquinone, nitro, naphthalimide and terephthalimide dyestuffs. Particularly preferred dyestuffs for such mixtures are, for example, the Colour Index dyestuffs Yellow 23, 42, 51, 59, 65, 71, 86, 108, 122, 163, 182, 211, Orange 29, 30, 32, 41, 44, 45, 61, 73, Red 60, 82, 86, 91, 92, 127, 134, 138, 159, 167, 191, 202, 258, 279, 284, 302, 323, Blue 27, 54, 56, 60, 73, 77, 79, 79:1, 87, 266, 333, 361, Violet 27, 28, 57 and 95, the weight ratios of the dyestuff mixtures depending on the desired colour shade.

EXAMPLES

Example 1

234.7 g (1.5 mol) of technical grade amino-imino-isoindolenine of the formula (V) (92.8% pure) and 235.5 g of cyanomethylbenzimidazole of the formula (VI), where $R^2$=hydrogen, were stirred with 3600 ml of methanol and the mixture was heated under reflux for 6 hours. The substance which had precipitated out was filtered off with suction at room temperature and washed with methanol and water. After drying, 363.5 g (84.9% of theory) of a product of the formula:

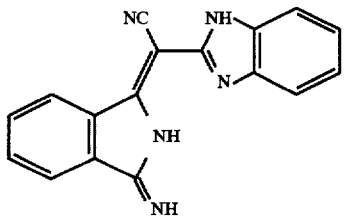

were obtained.

Example 2a 28.5 g of a substance prepared according to Example 1, 150 ml of n-butanol, 16.9 g of butyl cyanoacetate and 6 ml of glacial acetic acid were heated under reflux for 10 hours. After cooling to room temperature, the substance which had precipitated out was filtered off with suction and washed with methanol and water. After drying, 39.2 g of a product which, according to HPLC, contains 87.7% of a yellow dyestuff of the following formula in the form of long felt-like needles were obtained. The dyestuff dyed polyester fibres in yellow fluorescent shades with outstanding light-fastness.

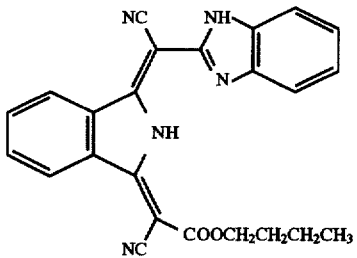

The substance obtainable by the process is in the β-modification and was purified by recrystallization in dimethylformamide at 80° C., and thereafter was in the γ-modification. (For data on the particular X-ray diffraction measurements, see the description).

Example 2b 28.5 g of a substance prepared according to Example 1, 150 ml of n-butanol, 16.9 g of butyl cyanoacetate and 7 g of glutaric acid were heated under reflux for 5 hours. After cooling to room temperature, the substance which had precipitated out was filtered off with suction and washed with methanol and water. After drying, 39.2 g of a product which, according to HPLC, contains 87.7% of a yellow dyestuff of the following formula in the form of compact crystals were obtained. The dyestuff dyed polyester fibres in yellow fluorescent shades with outstanding light-fastness.

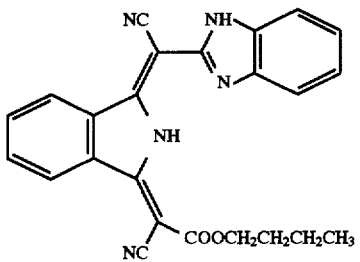

The substance obtainable by this process is in the co-modification. (For data on the particular X-ray diffraction measurements, see the description)

Example 3

32.8 g (0.21 mol) of technical grade amino-iminoisoindolenine of the formula (V) (92.8% pure), 31.4 g of cyanomethylbenzimidazole and 200 ml of n-butanol were heated at 60° C. for 1 hour. Thereafter, a further 100 ml of n-butanol, 36 g (0.25 mol) of butyl cyanoacetate and 12 ml of glacial acetic acid were added and the mixture was heated under reflux for 15 hours. The batch was worked up as in Example 2. 79.9 g of the same dyestuff as in Example 2 were obtained with a purity of 80.5%. The dyestuff was likewise in the β-modification.

Example 4

28.5 g (0.1 mol) of a substance prepared according to Example 1, 150 ml of N-methylpyrrolidone, 16.9 g (0.12 mol) of butyl cyanoacetate and 6 ml of glacial acetic acid were heated at 120° for 3 hours. After cooling to room temperature, 150 ml of water were added dropwise and the substance which had precipitated out was filtered off with suction and washed with methanol and water. 35.4 g of the same substance as in Example 2 were obtained. The dyestuff was in the γ-modification.

Example 5

36.8 g (0.24 mol) of technical grade amino-iminoisoindolenine (92.8% pure), 200 ml of water and 4.8 g of Reax® 910 (a medium-strength sulphonated kraft-lignin from Westvaco, USA), a dispersing agent based on sulpholignin, were stirred. 34.7 ml (0.24 mol) of butyl cyanoacetate were added dropwise at room temperature in the course of 10 minutes and the mixture was heated at 30° C. for 2 hours and at 40°, 60° and 70° for in each case 1 hour. Thereafter, 12 ml of glacial acetic acid and, in the course of about 30 minutes, 34.9 g (0.2 mol) of cyanomethylbenzimidazole are introduced and the mixture is heated at 70° C. for a further hour and at 90° C. for 3 hours. After filtration with suction and drying, 88.9 g of a preparation which, according to HPLC, contained 70.1% of the same dyestuff as in the case of Example 2 were obtained. The product is in the e-modification and could easily be comminuted by grinding in a bead mill and finished.

Finishing Example 1

5 g of ligninsulphonate, Na salt and 5 g of a nonionic dispersing agent (addition product of abietic acid and 50 mol equivalents of ethylene oxide) were added to 26 g of the dyestuff obtained in Example 5 (in the form of the water-moist press-cake) in 200 ml of water and the pH was brought to 7 with sulphuric acid. The dyestuff was then ground down to fine division (90%<1 µm) in a bead mill at room temperature for 1 hour, sieved and dried in a spray drier.

Finishing Example 2

The procedure was as in Finishing Example 1, but the 5 g of nonionic dispersing agent were replaced by 5 g of a surfactant mixture based on an alkoxylated styrene-phenol condensation product (phenol/styrene=2.8:1, 29 mol equivalents of ethylene oxide) and an inorganic ester thereof (amidosulphonic acid), which additionally contains a condensation product of oleic acid and 6.5 mol equivalents of ethylene oxide.

Use Example 1

2 g of tie powder obtained according to Finishing Example 1 were dispersed in 1000 g of water. 0.5 to 2 g/l of a commercially available dispersing agent based on a condensation product of naphthalenesulphonic acid sodium salt and formaldehyde, 0.5 to 2 g/l of monosodium phosphate and 2 g of a commercially available levelling auxiliary were added to tie dispersion and tie pH was brought to 4.5 to 5.5 with acetic acid. 100 g of a texurized polyester fabric based on polyethylene glycol terephthalate were introduced into tie dye liquor thus obtained and dyeing was carried out at 130° C. for 60 minutes.

Use Example 2

The dyestuff preparation obtained according to Finishing Example 2 was also used for dyeing in a manner analogous to Example 1.

Brilliant yellow dyeings of strong colour and with outstanding colouristic properties, such as light-fastness, were obtained, the heat stability of the dyestuff dispersion and the levelness of the dyeing from Use Example 2 being improved further.

The substances of the formula (II) listed in Table 1 were obtained with a comparable yield and purity when the procedure for the reaction was as in Example 2, but the analogous cyanoacetic acid esters and, as the solvent, the alcohols on which the esters are based were employed. The dyestuffs have the same colour shade.

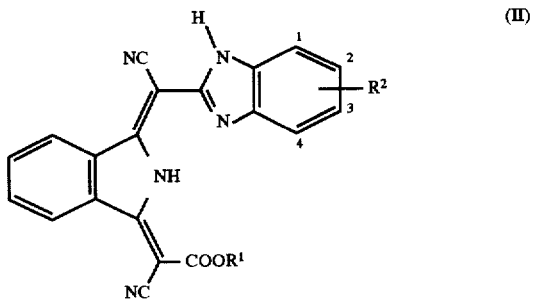

(II)

TABLE 1

| Example No. | R[1] | R[2]/position | Colour shade |
|---|---|---|---|
| Example 6 | —CH$_2$CH$_2$CH$_2$CH$_2$CH$_3$ | H | fluorescent yellow |
| Example 7 | —CH$_2$CH$_2$CH$_2$CH$_2$CH$_2$CH$_3$ | H | fluorescent yellow |
| Example 8 | —CH$_2$CH$_2$CH$_2$CH$_2$CH$_2$CH$_2$CH$_3$ | H | fluorescent yellow |
| Example 9 | —CH$_2$CH$_2$CH(CH$_3$)$_2$ | H | fluorescent yellow |
| Example 10 | —CH(C$_2$H$_5$)CH$_2$CH$_2$CH$_2$CH$_3$ | H | fluorescent yellow |
| Example 11 | —CH$_2$CH$_2$OCH$_2$CH$_3$ | H | fluorescent yellow |
| Example 12 | —CH$_2$CH$_2$OCH$_2$CH$_2$CH$_3$ | H | fluorescent yellow |
| Example 13 | —CH$_2$CH$_2$CH(CH$_3$)OCH$_3$ | H | fluorescent yellow |
| Example 14 | —CH$_2$CH$_2$CH$_2$CH$_3$ | —CH$_3$/3 | fluorescent orange |
| Example 15 | —CH$_2$CH$_2$CH$_2$CH$_3$ | —OCH$_3$/3 | fluorescent yellowish-tinged scarlet |
| Example 16 | —CH$_2$CH$_2$CH$_2$CH$_2$CH$_3$ | —OCH$_3$/3 | fluorescent yellowish-tinged scarlet |

Example 17

133.2 g (1 mol) of 2-amino-benzimidazole, 187.8 g (1.2 mol) of technical grade amino-imino-isoindolenine and 400 ml of formamide were heated at 70° C. for 10 hours. The mixture was allowed to cool to room temperature and the dyestuff was filtered off with suction and washed with methanol. After drying, 193.4 g (74% of theory) of a product of the formula:

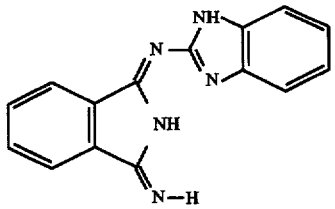

were obtained.

Example 18

26.1 g (0.1 mol) of a substance prepared according to Example 17 and 150 ml of n-butanol were stirred. Thereafter, 6 ml of glacial acetic acid and 17.3 ml (0.12 mol) of butyl cyanoacetate were added and the mixture was heated at 90° for 4 hours. The product which had precipitated out was filtered off with suction at room temperature and washed with methanol. After drying, 33.3 g of a yellow dyestuff of the following formula were obtained. The absorption maximum in dimethylformamide is at 419 nm.

The dyestuff dyes polyester in greenish-tinged yellow shades and shows an outstanding light-fastness and a high colour strength.

The substances of the formula (XIV) listed in Table 2 were obtained with a comparable yield and purity when the procedure for the reaction was as in Example 17 but the analogous cyanoacetic acid esters and, as the solvent, the alcohols on which the esters are based were employed. The dyestuffs have the same colour shade as the dyestuff of Example 15.

TABLE 2

| Example No. | $R^1$ |
|---|---|
| Example 19 | —$CH_2CH_2CH_2CH_2CH_3$ |
| Example 20 | —$CH_2CH_2CH_2CH_2CH_2CH_3$ |
| Example 21 | —$CH_2CH_2CH_2CH_2CH_2CH_2CH_3$ |
| Example 22 | —$CH_2CH_2CH(CH_3)_2$ |
| Example 23 | —$CH_2CH_2OCH_2CH_3$ |
| Example 24 | —$CH_2CH_2OCH_2CH_2CH_3$ |
| Example 25 | —$CH(CH_3)CH_2OCH_3$ |

What is claimed is:

1. A compound of the formula (I)

or a tautomeric form thereof, wherein

A represents N, and
$R^1$ represents a saturated or unsaturated, substituted or unsubstituted aliphatic radical having 5 to 20 C atoms, or A represents a cyanomethylene radical, and
$R^1$ represents a saturated or unsaturated, substituted or unsubstituted aliphatic radical having 5 to 20 C atoms which is uninterrupted or interrupted by one or more oxygen atoms and $R^2$ denotes hydrogen, halogen, $C_1$-$C_4$-alkyl, a saturated or unsaturated aliphatic oxyradical having I to 4 C atoms, which is unsubstituted or substituted by $C_1$-$C_4$-alkoxy, CN or $NO_2$.

2. The compound according to claim 1, which corresponds to the formula (II)

or a tautomeric form thereof, wherein $R^1$ represents a saturated or unsaturated aliphatic radical having 5 to 8 C atoms, which is unsubstituted or substituted and/or interrupted by one or more oxygen atoms.

3. The compound according to claim 1 of the formula (I) which corresponds to the formula (III)

or a tautomeric form thereof, wherein $R^1$ represents a saturated or unsaturated, unsubstituted or substituted aliphatic radical having 5 to 8 C atoms.

4. The compound according to claim 1, wherein $R^2$ denotes hydrogen.

5. The compound according to claim 1, wherein
A represents a cyanomethylene radical and
$R^1$ represents a saturated or unsaturated, substituted or unsubstituted aliphatic radical having 5 to 20 C atoms.

6. The compound according to claim 1, wherein $R^1$ represents an unsubstituted radical.

7. A compound according to claim 1, wherein A is N and $R^1$ is 6 to 20 C atoms.

8. A compound according to claim 7, wherein the compound is

9. A compound according to claim 1, wherein the compound is

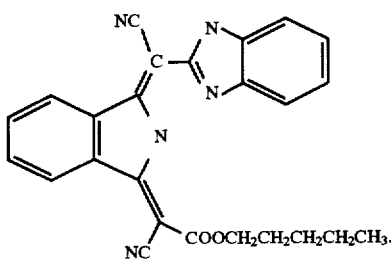

10. A compound of the formula (XV) or a tautomeric form thereof

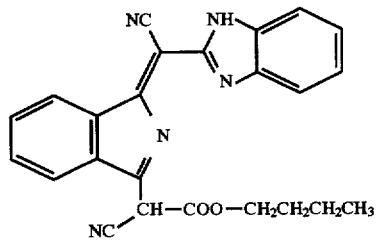

in the form of its α, γ- and/or ε-crystal modification, which are characterized by the following moderate to intense reflections in the X-ray diffraction diagram, the data denoting the distance between lattice planes and the associated relative intensities in per cent (figures in parentheses):

α-modification: 9.298 (100); 19.300 (12); 23.080 (14); 24.199 (20); 24.574 (36); 26.457 (85); 27.795 (23); 28.656 (16)

γ-modification: 5.007 (40); 5.474 (87); 6.316 (45.2); 8.393 (52); 10.045 (53); 16.646 (45); 25.772 (62); 26.377 (100)

ε-modification: 5.034 (50); 6.113 (100); 7.070 (29); 7.328 (25); 10.603 (33); 12.263 (23); 12.767 (21); 24.889 (24); 26.263 (30); 26.682 (23).

11. A process for dyeing and printing fully synthetic or semi-synthetic high molecular weight substances which comprises applying a compound according to claims 1 or 10 to said substances.

12. A mixture for dyeing automobile covering fabrics which comprises one or more compounds according to claim 1 and one or more dyestuffs which are used for dyeing automobile covering fabrics.

13. The process according to claim 11, wherein the substances are automobile covering fabrics.

14. A process for dyeing and printing automobile covering fabrics wherein a compound of the formula I

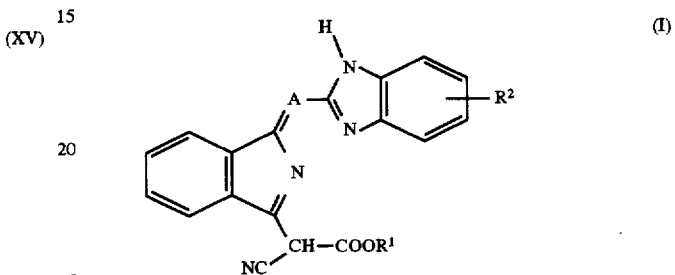

or a tautomeric form thereof, is applied, wherein
A represents N or a cyanomethylene radical,
$R^1$ represents a saturated or unsaturated, substituted or unsubstituted aliphatic radical having 6 C atoms, which is optionally interrupted by one or more oxygen atoms and
$R^2$ denotes hydrogen, halogen, $C_1$-$C_4$-alkyl, a saturated or unsaturated aliphatic oxyradical having 1 to 4 C atoms, which is unsubstituted or substituted by $C_1$-$C_4$-alkoxy, CN or $NO_2$.—

\* \* \* \* \*

UNITED STATES PATENT AND TRADEMARK OFFICE
CERTIFICATE OF CORRECTION

PATENT NO. : 5,741,911
DATED : April 21, 1998
INVENTOR(S) : Lorenz et al.

It is certified that error appears in the above-identified patent and that said Letters Patent is hereby corrected as shown below:

Title page,
Last line, delete " 14 " claims and substitute -- 19 --

Column 18,
Line 60, delete

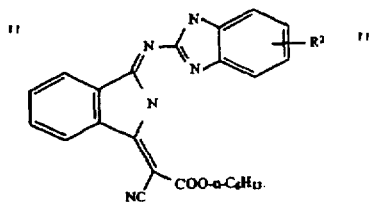

and substitute

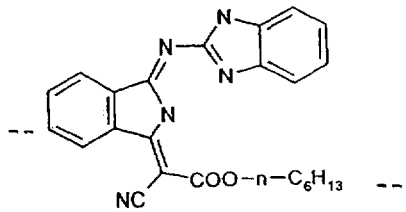

Column 20,
Line 35, after " claim 14... CN or $NO_2$. " insert
-- 15. A process for the preparation of a compound of the formula (I) according to claim 1 or a tautomeric form thereof, wherein a compound of the formula (IV)

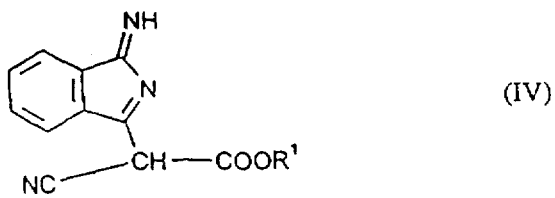  (IV)

is subjected to a condensation reaction with a benzeimidazole of the formula (V)

--

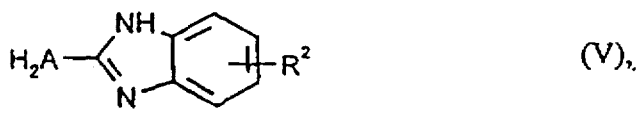  (V), or an aminoisoindolenine of the formula (VI)

UNITED STATES PATENT AND TRADEMARK OFFICE
CERTIFICATE OF CORRECTION

PATENT NO.   : 5,741,911
DATED        : April 21, 1998
INVENTOR(S)  : Lorenz et al.

It is certified that error appears in the above-identified patent and that said Letters Patent is hereby corrected as shown below:

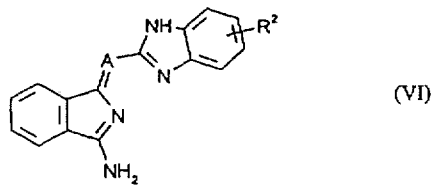

(VI)

is subjected to a condensation reaction with a cyanoacetic acid ester of the formula (VII)

NC-CH$_2$-COOR$^1$          (VII)

wherein
    R$^1$, R$^2$ and A have the meaning given in claim 1. --

--    16.   The process according to claim 15, wherein

A    represents a cyanomethylene radical. --

17.   A process for the preparation of a compound of the formula (I) according to claim 1 or a tautomeric form thereof

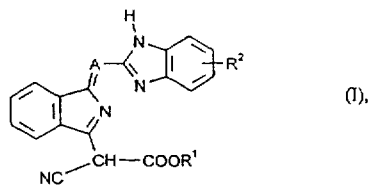

(I), wherein a compound of the formula (IV)

(IV),      --

--    is subjected to a condensation reaction with a benzimidazole of the formula (V)

UNITED STATES PATENT AND TRADEMARK OFFICE
CERTIFICATE OF CORRECTION

PATENT NO.    : 5,741,911
DATED         : April 21, 1998
INVENTOR(S)   : Lorenz et al.

It is certified that error appears in the above-identified patent and that said Letters Patent is hereby corrected as shown below:

(V), or an aminoisoindolenine of the formula (VI)

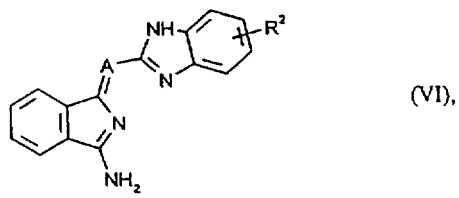

(VI), is subjected to a condensation reaction with a cyanoacetic acid ester of the formula (VII)

(VII)

wherein A, $R^1$ and $R^2$ have the meaning given in claim 1 in the presence of an organic acid. --

18. The process according to claim 17, wherein A represents a cyanomethylene radical. --

-- 19. The process according to claim 17, wherein the condensation is carried out in water or an aqueous medium. --

Signed and Sealed this

Ninth Day of April, 2002

Attest:

JAMES E. ROGAN
Attesting Officer    Director of the United States Patent and Trademark Office